US006451831B1

(12) United States Patent
Ienaga et al.

(10) Patent No.: US 6,451,831 B1
(45) Date of Patent: Sep. 17, 2002

(54) AGENT FOR HYPOALBUMINAEMIA

(75) Inventors: Kazuharu Ienaga, Osaka; Hiroki Mikami; Ryoji Nishibata, both of Hyogo, all of (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/074,772

(22) Filed: Feb. 12, 2002

(30) Foreign Application Priority Data

Feb. 13, 2001 (JP) ....................................... 2001/035262

(51) Int. Cl.⁷ ............................................. A61K 31/415

(52) U.S. Cl. ........................................ 514/389; 514/390

(58) Field of Search .................................. 514/389, 390

(56) References Cited

U.S. PATENT DOCUMENTS

| 3,818,031 A | 6/1974 | Baerlocher et al. |
| 4,096,130 A | 6/1978 | Kraft et al. |
| 4,281,009 A | 7/1981 | Konishi |
| 4,647,574 A * | 3/1987 | Ienaga et al. ............... 514/390 |
| 4,656,034 A | 4/1987 | Sarnoff |
| 4,658,830 A | 4/1987 | Sarnoff |
| 4,661,469 A | 4/1987 | Sarnoff |
| 4,683,240 A * | 7/1987 | Ienaga et al. ............... 514/390 |
| 4,772,585 A | 9/1988 | Sarnoff et al. |
| RE32,919 E | 5/1989 | Sarnoff |
| 4,832,682 A | 5/1989 | Sarnoff |
| 4,985,453 A | 1/1991 | Ishii et al. |
| 5,002,930 A | 3/1991 | Sarnoff et al. |
| 5,078,680 A | 1/1992 | Sarnoff |
| 5,084,473 A | 1/1992 | Mikami et al. |
| 5,340,829 A | 8/1994 | Clark et al. |
| 5,681,843 A | 10/1997 | Kotani et al. |
| 5,912,261 A | 6/1999 | Kotani et al. |
| 6,040,326 A | 3/2000 | Hotta et al. |
| 6,197,806 B1 | 3/2001 | Endou et al. |
| 6,251,929 B1 * | 6/2001 | Naiki et al. ................. 514/390 |

FOREIGN PATENT DOCUMENTS

| CH | 563 711 | 7/1975 |
| DE | 2 214 448 | 10/1972 |
| DE | 26 12 926 A1 | 10/1977 |
| EP | 0 780 125 A2 | 6/1977 |
| EP | 0 160 618 A1 | 11/1985 |
| EP | 0 194 226 A1 | 9/1986 |
| EP | 0 353 198 A1 | 1/1990 |
| EP | 0 412 940 A2 | 2/1991 |
| EP | 0 718 289 A1 | 6/1996 |
| EP | 0 718 290 A1 | 6/1996 |
| EP | 0 721 944 | 7/1996 |
| JP | 62-14 | 1/1987 |
| JP | 63-166870 | 7/1988 |
| JP | 64-56614 | 3/1989 |
| JP | 61-122275 | 6/1989 |
| JP | 2019363 | 1/1990 |
| JP | 2-040368 | 2/1990 |
| JP | 2-167264 | 6/1990 |
| JP | 2-225485 | 9/1990 |
| JP | 3-204874 | 9/1991 |
| JP | 6-135968 | 5/1994 |
| JP | 6-67827 | 8/1994 |
| JP | 6-305964 | 11/1994 |
| JP | 7-133264 | 5/1995 |
| JP | 8-157473 | 6/1996 |
| WO | WO 85/05103 | 11/1985 |
| WO | WO 86/01110 | 2/1986 |
| WO | WO 89/02890 | 4/1989 |

OTHER PUBLICATIONS

Miyanoshita et al., "Inhibitory Effect Of cyclic AMP On Phorbol Ester–Stimulated Production of Reactive Oxygen Metabolities In Rat Glomeruli", *Biochemical and Biophysical Research Communications*, vol. 165, No. 1, 1989, pp. 519–525.

Brownlee et al., "Aminoguanidine Prevents Diabetes–Induced Arterial Wall Protein Cross–Linking", *Science*, vol. 232, 1986, pp. 1629–1632.

Ishii et al., "Highly Selective Aldose Reductase Inhibitors", *J. Med. Chem.*, vol. 39, No. 9, 1996, pp. 1924–1927.

Kato et al., "Polyol Metabolism and Glycation in Diabetic Neuropathy", *Diabetes Frontier*, vol. 8, No. 4, 1997, pp. 510–511.

Kotani et al., "Highly Selective Aldose Reductase Inhibitors. 3.", *J. Med. Chem.*, vol. 40, No. 5, 1997, pp. 684–694.

Kotani et al., "Highly Selective Aldose Reductase Inhibitors, II", *Chem. Pharm. Bull*, vol. 45, No. 2, 1997, pp. 297–304.

Malamas et al., "Quinazolineacetic Acid and Related Analogues as Aldose Reductase Inhibitors", *J. Med. Chem.* (1991), 34, (4), 1492–503.

(List continued on next page.)

Primary Examiner—Raymond Henley, III
(74) Attorney, Agent, or Firm—Hollander Law Firm, P.L.C.

(57) ABSTRACT

A highly safe and useful therapeutic agent for hypoalbuminaemia contains a hydantoin derivative represented by the formula (I) or a pharmaceutically acceptable salt thereof as an effective ingredient:

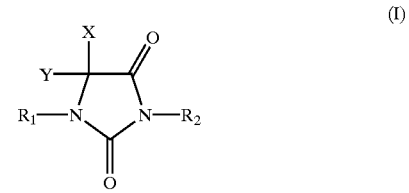

wherein each of $R_1$ and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group. Administration of the compounds substantially increases the serum albumin value of patients suffering from hypoalbuminaemia from abnormal values, and significantly improves the condition of hypoalbuminaemia.

24 Claims, No Drawings

OTHER PUBLICATIONS

CA60:532c, abstract (no date available).

Grangier, "Reactivity of Nucleophilic Uracil Derivatives", *J. Heterocyclic Chem.* (1994), 31, (6), 1707–14, abstract.

Kirsch, "Evidence for Free Radical Mechanisms of Brain Injury Resulting From Ischemia/Reperfusion–Induced Events," *Journal of Neurotrauma*, vol. 9, Supplement 1, 1992, pp. S157–S163.

Greenwald, "Therapeutic Usages of Oxygen Radical Scavengers In Human Diseases: Myths and Realities," *Free Rad. Res. Comms.*, vols. 12–13, pp. 531–538, 1991.

Greenwald, "Superoxide Dismutase and Catalase As Therapeutic Agents for Human Diseases," *Free Radical Biology & Medicine*, vol. 8, pp. 201–209, 1990.

Rice–Evans et al., "Current Status Of Antioxidant Therapy," *Free Radical Biology & Medicine*, vol. 15, pp. 77–96, 1993.

Kanazu et al., "Aldehyde reductase is a major protein associated with 3–deoxyglucosone reductase activity in rat, pig and human livers, " *Biochem J.*, 279, 903–906 (1991).

Flynn, "Aldehyde Reductases: Monomeric Nadph–Dependent Oxidoreductases With Multifunctional Potential," *Biochem. Pharmacol.*, vol. 31, No. 17, 2705–2712 (1982).

"Pathologic Biochemistry and Clinics of Free Radicals, Inflammation and Antiinflammation," *Nippon Rinsho*, vol. 36, No. 10, pp. 93–97 (1988).

Yonezawa et al., *Nippon Kagaku Zasshi*, 89, No. 8, pp. 62–64 (1968).

Patton, "Reactions of Isocyanates with Cyanohydrins. The Synthesis of 2,4–Oxazolidinediones and 1,3–Disubstituted Parabanic Acids", *J. Org. Chem.*, 32, No. 2, pp. 383–388 (1967).

K. Ogawva, et al., "Syntheses of substituted, 2,4–dioxo–thienopyrimidin–1–acetic acids and their evaluation as aldose reductase inhibitors", *European Journal of Medicinal Chemistrychimica Therapeutica*, vol. 28, No. 10, 1993, pp. 769–781.

Morrison and Boyd, *Organic Chemistry*, Allyn and Bacon, Inc., Boston (1965), pp. 806,808,847–848.

White, R. H., et al., "Hypertension, Hyperreninemia, and secondard Hyeraldosteronism in Systemic Necrotizing Vasculitis", *Annuals of Internal Medicine*, US, New York, NY, vol. 92, No. 2, Part 01, Feb. 1980, pp. 199–201, XP000856338.

Krasnov et al. (CA 119:8771), abstract of *ZH. Org. Khim.* (1992), 28(7), 1531–7.

Ishii et al. abstract of JP 05043555) 1993.

Henmi et al. (CA 113:23919), abstract of JP 02019363) 1990.

European Search Report for EP 97122861, published May 15, 1998.

* cited by examiner-

AGENT FOR HYPOALBUMINAEMIA

FIELD OF THE INVENTION

The present invention relates to an improving agent for hypoalbuminaemia containing a hydantoin derivative or a pharmaceutically acceptable salt thereof as an effective ingredient.

BACKGROUND OF THE INVENTION

The concentration of serum albumin is 3.5-5.5 g/dL in healthy subjects. When the concentration is lowered to less than 3.5 g/dL, such condition is diagnosed as hypoalbuminaemia. Serious hypoalbuminaemia with less than 3.0 g/dL of serum albumin concentration is clinically significant. Hypoalbuminaemia causes symptoms such as edema and ascites, and worsens disorders by hyperbilirubinemia. This disease occurs from various causes such as a decrease in albumin synthesis, loss of albumin from blood and dilution of plasma. Albumin is synthesized only by hepatocytes and a decrease in their synthesis causes hypoalbuminaemia. The main causes of a decrease in the synthesis of albumin are a deficiency of amino acid supply by nutrition disorders and a lowered ability for albumin synthesis by hepatic disease. The loss of albumin from blood is caused by renal failure such as nephritic syndrome, traumatic injury such as burn and protein-losing gastroenteropathy. Dilution of plasma owing to heart failure, accelerated catabolism by hyperthyroidism and the like also cause hypoalbuminaemia. As a remedy for hypoalbuminaemia, dietetic therapy using a high protein diet and drug therapy by total amino acid preparations have been performed. However, in the case of intravenous administration of amino acids, caution is needed against an exhibition of side effects such as acid-base balance disorder, hyperammonaemia, imbalance of amino acids and azotemia. Also, when blood protein preparations are used, there are characteristic problems with such preparations such as contamination with virus.

As mentioned above, amino acid preparations and blood preparations for intravenous administration are mainly used at present as a therapeutic drug for hypoalbuminaemia. There is a strong demand in the clinical field for a therapeutic agent having higher safety and which can be orally administrated.

Several hydantoin compounds of the present invention were found as novel substances having plant growth controlling action. As a result of investigations thereafter for the compounds including analogs thereof, they have been found to have pharmacological actions such as hypoglycemic and hypolipemic actions, and also exhibit low toxicity resulting in almost no side effects. See U.S. Pat. Nos. 4,647,574 and 4,683,240, each to Ienaga et al, and Japanese Laid-Open Patent Publications Sho-57/114578, Sho-60/188373, Sho-61/122275, Sho-62/45525, Sho-62/14, Hei-01/75473, Hei-01/299276, etc.). It has been also disclosed that the compounds of the present invention are useful as: 1) agents for lowering uremic toxin (Japanese Laid-Open Patent Publication Hei-03/72463), 2) eliminating agents of active oxygen and free radicals (Japanese Laid-Open Patent Publication Hei-09/227377), and 3) therapeutic agents for intractable vasculitis (Japanese Laid-Open Patent Publication 2000/212083 and U.S. Pat. No. 6,251,929 B1). However, the therapeutic effect of the compounds of the present invention for hypoalbuminaemia has not ever been found.

The present inventors have carried out intensive investigations and have found that the hydantoin derivatives of the present invention have a therapeutic effect for hypoalbuminaemia whereupon the present invention has been accomplished. The compounds of the present invention are less toxic and have almost no side effect, and accordingly they are quite useful as an improving agent for hypoalbuminaemia having higher safety and are capable of oral administration.

The present invention solves the above-mentioned problems and provides a highly safe therapeutic agent for hypoalbuminaemia which can be oral administration.

SUMMARY OF THE INVENTION

The hydantoin derivatives and their pharmaceutically acceptable salts of the present invention may be us ed as therapeutic agents for the treatment of hypoalbuminaemia in patients known to be in need of such treatment. In embodiments of the present invention patients may be treated for hypoalbuminaemia caused by: 1) a deficiency of amino acid supply caused by nutrition disorders, 2) a lowered ability for albumin synthesis due to hepatic disease, 3) loss of albumin from blood due to renal failure such as nephritic syndrome, 4) traumatic injury such as burn, 5) protein-losing gastroenteropathy, 6) dilution of plasma owing to heart failure, and 7) accelerated catabolism by hyperthyroidism, and the like.

The pharmaceutical compositions employed in the present invention include at least one hydantoin derivative represented by the general formula (I) or pharmaceutically acceptable salts of the derivatives represented by the general formula (I):

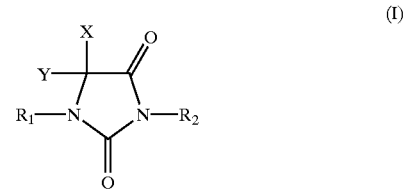

wherein each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together represent an oxo group.

The hydantoin derivatives and their pharmaceutically acceptable salts may be administered orally or parenterally to patients in need of treatment in pharmaceutically effective amounts with little, if any side effects, low toxicity, and high safety to substantially increase serum albumin levels or values in patients diagnosed with hypoalbuminaemia.

DETAILED DESCRIPTION OF THE INVENTION

The effective ingredient of the improving agent for hypoalbuminaemia according to the present invention is a hydantoin derivative represented by the following formula (I) or a pharmaceutically acceptable salt thereof:

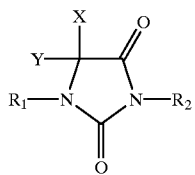

(I)

wherein each of $R_1$ and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group.

In the above mentioned formula (I), each of $R_1$ and $R_2$, which may be the same or different, represents hydrogen, an alkyl group, preferably a straight or branched alkyl group having 1 to 20 carbon atoms such as methyl, ethyl, propyl, isopropyl, butyl, isobutyl, sec-butyl, t-butyl, pentyl, isopentyl, neopentyl, t-pentyl, hexyl, dimethylbutyl, heptyl, octyl, nonyl, decyl or stearyl; or a cycloalkyl group, preferably a cycloalkyl group having 3 to 8 carbon atoms such as cyclopropyl, cyclobutyl, cyclopentyl, cyclohexyl, cycloheptyl or cyclooctyl.

Each of X and Y, which may be the same or different, represents hydrogen, a hydroxyl group, an alkyl group, preferably a straight or branched alkyl group having 1 to 3 carbon atoms such as methyl, ethyl, propyl, isopropyl; or an alkoxy group, preferably a straight or branched alkoxy group having 1 to 5 carbon atoms such as methoxy, ethoxy, propoxy, isopropoxy, butoxy, isobutoxy, sec-butoxy, t-butoxy, pentoxy, isopentoxy, neopentoxy; or X and Y together represent an oxo group.

Preferred compounds of the present invention are:
[Compound 1] Hydantoin
[Compound 2] 1-Methylhydantoin
[Compound 3] 3-Methylhydantoin
[Compound 4] 1-Ethylhydantoin
[Compound 5] 1-Propylhydantoin
[Compound 6] 1-Butylhydantoin
[Compound 7] 1-t-Butylhydantoin
[Compound 8] 1-Hexylhydantoin
[Compound 9] 1-(1,3-Dimethylbutyl)hydantoin
[Compound 10] 1-Decylhydantoin
[Compound 11] 1-Stearylhydantoin
[Compound 12] 1,3-Dimethylhydantoin
[Compound 13] 1,5-Dimethylhydantoin
[Compound 14] 3,5-Dimethylhydantoin
[Compound 15] 1-Cyclopentylhydantoin
[Compound 16] 1-Cyclohexylhydantoin
[Compound 17] 1-Cyclohexyl-3-methylhydantoin
[Compound 18] 3-Cyclohexylhydantoin
[Compound 19] 1,3-Dicyclohexylhydantoin
[Compound 20] 5-Hydroxyhydantoin
[Compound 21] 5-Hydroxy-1-methylhydantoin
[Compound 22] 5-Hydroxy-3-methylhydantoin
[Compound 23] 5-Hydroxy-1-ethylhydantoin
[Compound 24] 5-Hydroxy-1-propylhydantoin
[Compound 25] 5-Hydroxy-1-butylhydantoin
[Compound 26] 5-Hydroxy-1-t-butylhydantoin
[Compound 27] 5-Hydroxy-1-hexylhydantoin
[Compound 28] 5-Hydroxy-1-(1,3-dimethylbutyl)hydantoin
[Compound 29] 5-Hydroxy-1-decylhydantoin
[Compound 30] 5-Hydroxy-1-stearylhydantoin
[Compound 31] 5-Hydroxy-1-cyclopentylhydantoin
[Compound 32] 5-Hydroxy-1-cyclohexylhydantoin
[Compound 33] 5-Hydroxy-1-cyclohexyl-3-methylhydantoin
[Compound 34] 5-Hydroxy-1,3-dimethylhydantoin
[Compound 35] 5-Hydroxy-1,5-dimethylhydantoin
[Compound 36] 5-Hydroxy-3,5-dimethylhydantoin
[Compound 37] 5-Hydroxy- 1,3-dicyclohexylhydantoin
[Compound 38] 5-Methoxyhydantoin
[Compound 39] 5-Methoxy-1-methylhydantoin
[Compound 40] 5-Methoxy-3-methylhydantoin
[Compound 41] 5-Methoxy-1-ethylhydantoin
[Compound 42] 5-Methoxy-1-propylhydantoin
[Compound 43] 5-Methoxy-1-butylhydantoin
[Compound 44] 5-Methoxy-1-cyclohexylhydantoin
[Compound 45] 5-Methoxy-3-cyclohexylhydantoin
[Compound 46] 5-Ethoxyhydantoin
[Compound 47] 5-Ethoxy-1-methylhydantoin
[Compound 48] 5-Ethoxy-3-methylhydantoin
[Compound 49] 5-Ethoxy-1-ethylhydantoin
[Compound 50] 5-Ethoxy-1-propylhydantoin
[Compound 51] 5-Ethoxy-1-butylhydantoin
[Compound 52] 5-Propoxyhydantoin
[Compound 53] 5-Propoxy-1-methylhydantoin
[Compound 54] 5-Propoxy-3-methylhydantoin
[Compound 55] 5-Propoxy-1-ethylhydantoin
[Compound 56] 5-Propoxy-1-propylhydantoin
[Compound 57] 5-Propoxy-1-butylhydantoin
[Compound 58] 5-Butoxyhydantoin
[Compound 59] 5-Butoxy-1-methylhydantoin
[Compound 60] 5-Butoxy-3-methylhydantoin
[Compound 61] 5-t-Butoxyhydantoin
[Compound 62] 5-t-Butoxy-1-methylhydantoin
[Compound 63] 5-t-Butoxy-3-butylhydantoin
[Compound 64] Imidazolidinetrione
[Compound 65] 1-Methylimidazolidinetrione
[Compound 66] 1-Ethylimidazolidinetrione
[Compound 67] 1-Butylimidazolidinetrione
[Compound 68] 1-Isobutylimidazolidinetrione
[Compound 69] 1-t-Butylimidazolidinetrione
[Compound 70] 1-Hexylimidazolidinetrione
[Compound 71] 1-(1,3-Dimethylbutyl)imidazolidinetrione
[Compound 72] 1-Decylimidazolidinetrione
[Compound 73] 1-Cyclopentylimidazolidinetrione
[Compound 74] 1-Cyclopentyl-3-ethylimidazolidinetrione
[Compound 75] 1-Cyclohexylimidazolidinetrione
[Compound 76] 1,3-Dimethylimidazolidinetrione
[Compound 77] 1,3-Dicyclohexylimidazolidinetrione The hydantoin derivatives of the present invention include the pharmaceutically acceptable salts of the compounds represented by the above given formula (I). Exemplary salts of the present invention are acid addition salts of the hydantoin derivatives of general formula (I) with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, or sulfanilic acid. Other salts of the present invention include salts of the hydantoin derivatives of general formula (I) with: a) an alkali metal such as sodium and potassium, b) an alkaline-earth metal such as calcium, magnesium and barium, and c) other metals such as aluminum and zinc.

The pharmaceutically acceptable salts may be manufactured by conventional methods, starting from the hydantoin derivatives of the present invention in a free state or free form, or by conversion from one salt to another salt.

When there are steric isomers or stereoisomers such as cis-trans isomers, optical isomers, or conformational isomers, hydrates or complexes for the compounds of the present invention, the present invention includes any and all of such isomers, hydrates and complexes.

The compounds of the present invention may be manufactured by conventional methods as disclosed, for example, in Japanese Laid Open (Kokai) Nos. 61/122275 (published Jun. 10, 1986) and 62/14 (published Jan. 6, 1987) and their corresponding U.S. Pat. Nos. 4,647,574 and 4,683,240 each to Ienaga et al, respectively. The disclosures of each of said Japanese publications and U.S. Pat. Nos. 4,647,574 and 4,683,240 are herein incorporated by reference in their entireties. For example, hydantoin derivatives of the present invention may be produced by methods as disclosed in U.S. Pat. No. 4,647,574 at column 2 line 39 to column 3 line 32. Thus, the hydantoin derivatives may be produced by first conventionally esterifying a glyoxylic acid. For example, a glyoxylic acid is reacted with an alcohol or 2-methoxyethanol, at room temperature or at a suitable temperature above room temperature or under reflux, for about several hours to about a day, with the produced water being removed, in the presence of an organic acid catalyst such as p-toluene-sulfonic acid or camphorsulfonic acid in an aprotic solvent such as benzene, toluene, xylene or carbon tetrachloride. Then the produced glyoxylic acid ester or an o-alkylglyoxylic acid ester (glyoxylic acid ester alcoholate) is, without being isolated or further purified, reacted at room temperature or heated under reflux for about 1 hour to about several days with, e.g., N-alkylurea, N-cycloalkylurea, N,N'dialkylurea or N,N'-dicycloalkylurea in an appropriate solvent such as water, acetic acid or alcohol, such as butanol or mixtures thereof, to give compounds of the present invention represented by the general formula (I).

The above-mentioned reaction can also be carried out with an α-ketocarbonic acid such as pyruvic acid as the starting material instead of a glyoxylic acid.

The compounds of the present invention wherein X or Y is an alkoxy group may be produced from a hydantoin derivative as prepared, e.g., by the process described above, by a conventional O-alkylation process. The hydantoin derivatives may be reacted with p-toluenesulfonyl chloride or mesyl chloride to introduce a removable residue into the hydroxy group at the 5-position, in the presence of an organic base such as a lower alkylamine or an alkali metal alkoxide in an appropriate solvent which does not inhibit the reaction. During or after the reaction, the resultant product is reacted with the alcohol corresponding to the X or Y substituent of the desired hydantoin derivative to give the compound of the present invention. This O-alkylation may be carried out at room temperature or at a suitable temperature above room temperature or under reflux, for about several hours to about several days.

The compounds of the present invention also include products from the N-alkylation of the hydantoin derivatives. The hydantoin derivative is reacted with a halogenated alkyl, a halogenated cycloalkyl, a dialkylsulfuric acid such as dimethylsulfonic acid, a p-toluenesulfonic acid alkyl ester or a p-toluenesulfonic acid cycloalkyl ester, in the presence of a base such as a lower alkyl amine, an alkali metal alkoxide or a hydroxyalkyl metal in an appropriate solvent which does not inhibit the reaction such as absolute alcohol, or dimethyl sulfoxide. The N-alkylation may be carried out at room temperature or at a suitable temperature above room temperature for about several hours to about several days.

When X and Y represent an oxo group, the hydantoin derivatives or imidazolidinetrione derivatives of the present invention may be produced by methods as disclosed in T. Yonezawa et al, *Nippon Kagaku Zasshi*, 89, No. 8, pp 62–64 (1968), Tad L. Patton, *J. Org. Chem.*, 32, No. 2, 383–388 (1967), and U.S. Pat. No. 4,683,240 at column 3 lines 27–49. For example, as disclosed in U.S. Pat. No. 4,683,240, oxalyl chloride and an N-substituted urea, such as an N-alkylurea, or N-cycloalkylurea may be stirred in an appropriate solvent such as tetrahydrofuran which does not inhibit the reaction in an ice-water bath or at room temperature. Alternatively, diethyl oxalate and the above-mentioned N-substituted urea may be stirred in an appropriate solvent which does not inhibit the reaction in the presence of an organic base such as an amine or alkali metal alkoxide at room temperature, if desired, by heating to higher temperatures to give the imidazolidinetrione derivatives of the present invention.

The compounds of the invention can also be prepared by conventional N-alkylation wherein unsubstituted, 1-alkylsubstituted or 1-cycloalkylsubstituted imidazolidin-etrione is reacted with halogenated alkyl.

The compounds of the present invention prepared as described above may be purified by conventional methods such as distillation, chromatography and recrystallization. The compounds may be identified by means of, for example, elementary analysis, melting point measurement, infrared (IR), nuclear magnetic resonance (NMR), ultraviolet (UV), and mass spectroscopy (MS).

The compounds of the present invention, which include the hydantoin derivatives and their pharmaceutically acceptable salts and complexes, can be made into pharmaceutical preparations by combining one or more of the compounds with at least one pharmaceutically acceptable carrier or diluent. Any of the known methods for providing preparations, such as for oral administrations (e.g. tablets, capsules, powders, liquids, etc.) and for parenteral administrations (e.g. for subcutaneous, intravenous, intramuscular, intrarectal and intranasal administrations) may be used to produce the pharmaceutical compositions of the present invention. In preparing the preparations, the hydantoin derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, hydroxypropylcellulose, etc.), gum arabicum, corn starch, gelatin, etc., (2) disintegrating agents such as corn starch, potato starch, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

It is also possible, depending upon the type of the disease, to prepare pharmaceutical preparations other than the above-mentioned ones which are suitable for therapy depending upon the state of the patient. Exemplary of other pharmaceutical preparations are syrups, suppositories, inhalations, aerosol preparations, collyriums, medicines for external use (e.g. ointments, gels, poultices), etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 1–1,000 mg per day, preferably 5–600 mg per day, to common adults. In the case of a parenteral administration such as by injection, the preferred dosage, may be from $\frac{1}{3}$ to $\frac{1}{10}$ of the above-mentioned oral dosages because of the effects of absorption, etc. in the oral route.

Preferred embodiments of the improving agent for hypoalbuminaemia of the present invention containing the compound represented by the above formula (I) are:

(1) A improving agent for hypoalbuminaemia containing the compound represented by the formula (I) wherein one of X and Y represents hydrogen as an active ingredient.

(2) An agent according to the above subparagraph (1) wherein the other of X and Y represents a hydroxyl group.

(3) An agent according to the above subparagraph (2) wherein one of $R_1$ and $R_2$ represents an alkyl group and the other represents hydrogen.

(4) An agent according to the above subparagraph (3) wherein $R_1$ represents an alkyl group.

(5) An agent according to the above subparagraph (4) wherein $R_1$ represents an alkyl group having 1 to 4 carbon atoms.

(6) An agent according to the above subparagraph (5) wherein $R_1$ represents methyl.

(7) An agent according to one of the above subparagraphs (1)–(6) which is used for the therapy of hypoalbuminaemia owing to hepatic disease.

(8) An agent according to one of the above subparagraphs (1)–(6) which is used for the therapy of hypoalbuminaemia owing to nutrition disorders.

(9) An agent according to one of the above subparagraphs (1)–(6) which is used for the therapy of hypoalbuminaemia owing to renal failure.

(10) An agent according to one of the above subparagraphs (1)–(6) which is used for the therapy of hypoalbuminaemia owing to traumatic injury.

(11) An agent according to one of the above subparagraphs (1)–(6) which is used for the therapy of hypoalbuminaemia owing to protein- losing gastroenteropathy.

(12) An agent according to one of the above subparagraphs (1)–(6) which is used for the therapy of hypoalbuminaemia owing to heart failure.

(13) An agent according to one of the above subparagraphs (1)–(6) which is used for the therapy of hypoalbuminaemia owing to hypercatabolism.

The most preferred compound for use in the present invention, which has been clinically confirmed as having low toxicity and lower side effects is 5-hydroxy-1-methylhydantoin (Compound 21).

The present invention is illustrated by the following non-limiting example wherein all parts, percentages and ratios are by weight, unless indicated to the contrary:

EXAMPLE

In this example, the unexpected increase in albumin values in patients in need of treatment for hypoalbuminaemia is demonstrated by the results of a clinical test.

The compound of the present invention (Compound 21 ) was administered to 6 patients suffering from hypoalbuminaemia (serum albumin value was less than 3.0 g/dL) at the dose of 200 mg/day (dosage for only Patient 1 was 400 mg/day). Serum albumin values were compared between before and after administration for 24 weeks (after 16 weeks in case of only Patient 2). The result wherein a significant difference was statistically analyzed by a paired t-test is shown in Table 1. The serum albumin values were significantly increased by the administration of the compound of the present invention and, therefore, it showed an improving effect for hypoalbuminaemia. In another case of tested subjects showing a normal value of serum albumin, any change of the value was not noted by the administration of the compounds of the present invention.

TABLE 1

|  | Before Administration | After Administration for 24 weeks |
| --- | --- | --- |
| Patient 1 | 1.7 g/dL | 2.1 g/dL |
| Patient 2 | 2.0 g/dL | 2.3 g/dL |
| Patient 3 | 2.3 g/dL | 3.4 g/dL |
| Patient 4 | 2.4 g/dL | 2.7 g/dL |
| Patient 5 | 2.5 g/dL | 3.2 g/dL |
| Patient 6 | 2.7 g/dL | 3.0 g/dL |
| Mean Value | 2.3 ± 0.2 g/dL | 2.8 ± 0.2* g/dL |

$p < 0.01$

It is apparent from the above-mentioned clinical test that the administration of the compound of the present invention gave an increase of serum albumin value in patients suffering from hypoalbuminaemia and, therefore, an improving effect of the compound of the present invention for hypoalbuminaemia was shown. Consequently, the compounds of the present invention are very useful as a therapeutic agent for hypoalbuminaemia. The compounds of the present invention do not affect subjects with normal values of serum albumin, and therefore it is considered that the compounds of this invention show an effect only in a morbid or diseased state wherein the serum albumin value is abnormally lowered. In addition, it has been shown by both animal and clinical tests that the compounds of the present invention have little side effect. Thus, the compounds of the present invention have both high safety and therapeutic effect, and accordingly, the compounds of this invention are very useful as a drug for hypoalbuminaemia available for oral and long-term administration.

In embodiments of the invention, hypoalbuminaemia and diseases or conditions which cause it may be treated in a patient in need of such treatment by measuring the serum albumin, determining whether the serum albumin level of the patient is present at an abnormal level, for example below about 3.5 g/dL, generally below about 3.0 g/dL, and administering a hydantoin derivative of the present invention to increase the albumin level to a normal level so as to alleviate symptoms of the disease or condition. In embodiments of the present invention, at least one hydantoin derivative may administered to substantially increase the serum album value of a patient, for example from an abnormally low value of less than or equal to 2.5 g/dL to a value of at least 3.0 g/dL, preferably at least 3.5 g/dL.

Accordingly, the hydantoin derivatives of the present invention may be employed in accordance with the present invention for the treatment of diseases or conditions other than diabetes, diabetic complications, intractable vasculitis, and those requiring hypoglycemic or hypolipemic action, or lowering of uremic toxin. Thus, the hydantoin derivatives of the present invention may be used for the treatment of diseases or conditions which cause hypoalbuminaemia, such as nutrition disorders, hepatic disease, renal failure, such as nephritic syndrome, traumatic injury such as burn protein-losing gastroenteropathy, heart failure, accelerated catabolism by hyperthyroidism, and the like by substantially increasing serum albumin levels from abnormally low levels to near normal or normal levels.

What is claimed is:

1. A method for the treatment of hypoalbuminaemia comprising administering to a patient in need of such treatment a pharmaceutically effective amount of at least one hydantoin derivative represented by the formula (I) or a pharmaceutically acceptable salt, hydrate or complex thereof, said hydantoin derivative being represented by the formula (I):

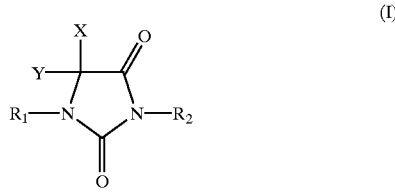

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

2. A method as claimed in claim 1 wherein one of X and Y is hydrogen.

3. A method as claimed in claim 2 wherein the other of X and Y is a hydroxyl group.

4. A method as claimed in claim 3 wherein one of $R_1$ and $R_2$ is an alkyl group and the other is hydrogen.

5. A method as claimed in claim 4 wherein $R_1$ is alkyl.

6. A method as claimed in claim 5 wherein $R_1$ is an alkyl having 1 to 4 carbon atoms.

7. A method as claimed in claim 6 wherein $R_1$ is methyl.

8. A method as claimed in claim 1 wherein said hypoalbuminaemia is caused by hepatic disease.

9. A method as claimed in claim 1 wherein said hypoalbuminaemia is caused by a nutrition disorder.

10. A method as claimed in claim 1 wherein said hypoalbuminaemia is caused by renal failure.

11. A method as claimed in claim 1 wherein said hypoalbuminaemia is caused by traumatic injury.

12. A method as claimed in claim 1 wherein said hypoalbuminaemia is caused by protein-losing gastroenteropathy.

13. A method as claimed in claim 1 wherein said hypoalbuminaemia is caused by heart failure.

14. A method as claimed in claim 1 wherein said hypoalbuminaemia is caused by hypercatabolism.

15. A method as claimed in claim 1 wherein said at least one hydantoin derivative is administered to substantially increase the serum album value of said patient to at least 3.0 g/dL.

16. A method for treating hypoalbuminaemia comprising administering to a patient in need of such treatment a pharmaceutical composition comprising a pharmaceutically effective amount of at least one hydantoin derivative represented by the formula (I) or a pharmaceutically acceptable salt, hydrate or complex thereof, and a pharmaceutically acceptable carrier, said hydantoin derivative being represented by the formula (I):

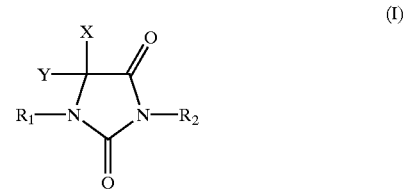

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

17. A method as claimed in claim 16 wherein one of X and Y is hydrogen.

18. A method as claimed in claim 17 wherein the other of X and Y is a hydroxyl group.

19. A method as claimed in claim 18 wherein one of $R_1$ and $R_2$ is an alkyl group and the other is hydrogen.

20. A method as claimed in claim 19 wherein $R_1$ is methyl.

21. A method as claimed in claim 12 wherein said hypoalbuminaemia is caused by a disease or condition selected from the group consisting of nutrition disorders, hepatic disease, renal failure, traumatic injury, protein-losing gastroenteropathy, heart failure, and accelerated catabolism by hyperthyroidism.

22. A method for the treatment of hypoalbuminaemia comprising determining the serum albumin value of a patient and administering to a patient in need of such treatment a pharmaceutically effective amount of at least one hydantoin derivative represented by the formula (I) or a pharmaceutically acceptable salt, hydrate or complex thereof to substantially increase the serum albumin value, said hydantoin derivative being represented by the formula (I):

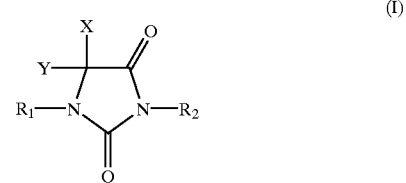

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

23. A method as claimed in claim 22 wherein said hypoalbuminaemia is caused by a disease or condition selected from the group consisting of nutrition disorders, hepatic disease, renal failure, traumatic injury, protein-losing gastroenteropathy, heart failure, and accelerated catabolism by hyperthyroidism.

24. A method as claimed in claim 23 wherein said at least one hydantoin derivative is administered to substantially increase the serum album value of said patient to at least 3.0 g/dL.

* * * * *